United States Patent
Owens

(10) Patent No.: US 6,525,820 B1
(45) Date of Patent: Feb. 25, 2003

(54) RAYLEIGH SCATTERING OPTICAL FLUX MONITOR

(75) Inventor: Dale W. Owens, Minnetonka, MN (US)

(73) Assignee: Gradient Technology, Blaine, MN (US)

(*) Notice: Subject to any disclaimer, the term of this patent is extended or adjusted under 35 U.S.C. 154(b) by 0 days.

(21) Appl. No.: 09/474,959

(22) Filed: Dec. 30, 1999

(51) Int. Cl.[7] .................................................. G01B 9/02
(52) U.S. Cl. ...................................... 356/450; 356/517
(58) Field of Search ............................... 356/450, 517, 356/345

(56) References Cited

U.S. PATENT DOCUMENTS

| | | | |
|---|---|---|---|
| 4,812,650 A | 3/1989 | Eckstein | 250/307 |
| 5,121,988 A | * 6/1992 | Blesener et al. | 356/442 |
| 5,171,399 A | 12/1992 | Brennan et al. | 156/601 |
| 5,397,895 A | 3/1995 | Leone et al. | 250/288 |
| 5,556,462 A | 9/1996 | Celii et al. | 117/85 |
| 5,598,260 A | 1/1997 | Brewer et al. | 356/72 |

* cited by examiner

Primary Examiner—Frank G. Font
Assistant Examiner—Philip Natividad
(74) Attorney, Agent, or Firm—Henry E. Naylor

(57) ABSTRACT

A device for in situ real time monitoring of atomic and molecular fluxes by use Rayleigh scattering. The flux can be generated by an effusion cell during molecular beam epitaxy. The present device uses a coherent light source, such as a helium neon laser, a high precision mirror assembly capable of providing an effective number of reflections though the flux beam and an interferometer detector to track the changes in flux.

52 Claims, 1 Drawing Sheet

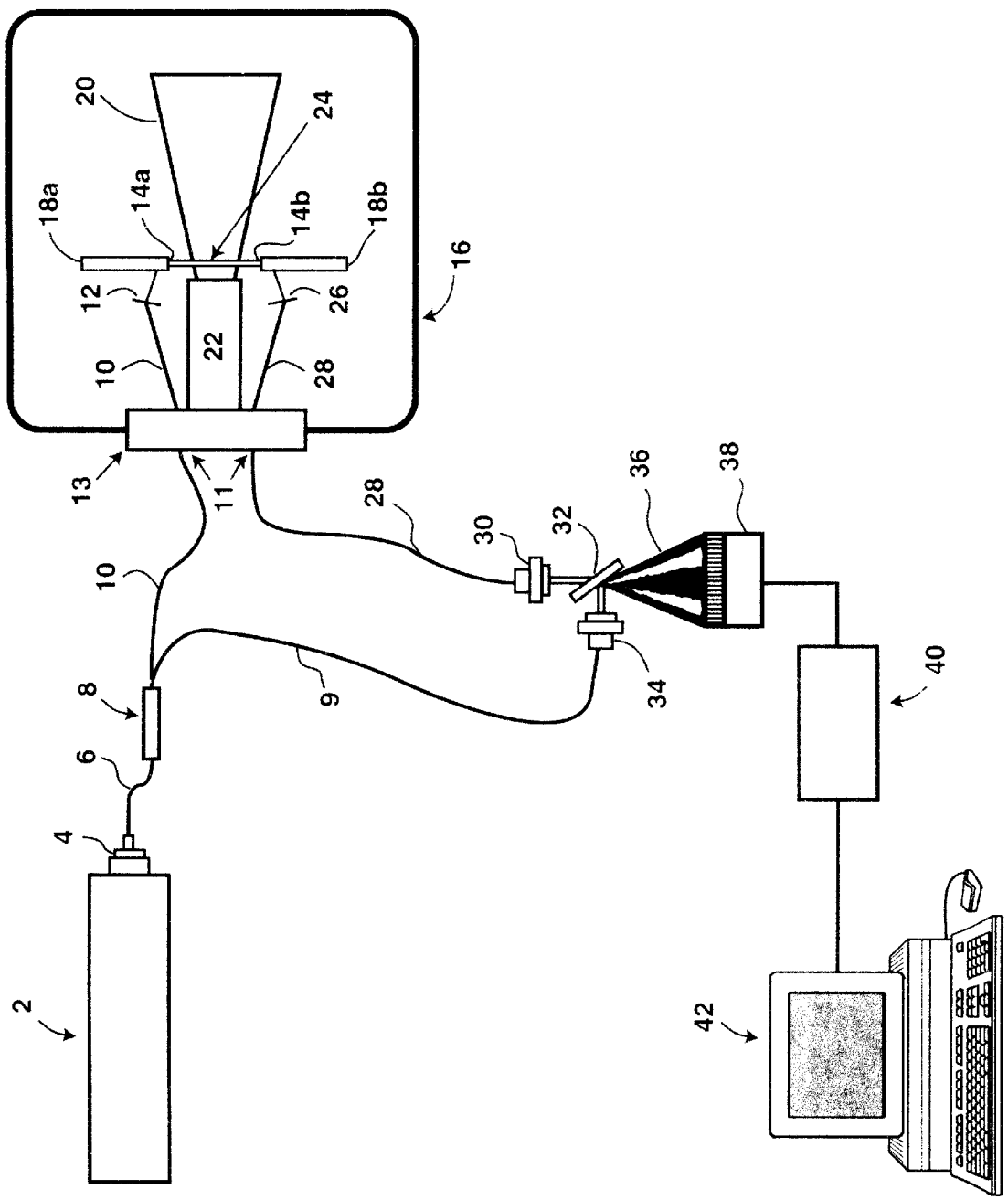

RAYLEIGH SCATTERING OPTICAL FLUX MONITOR

FIELD OF THE INVENTION

The present invention relates to an apparatus for in situ real time monitoring of atomic and molecular fluxes by using Rayleigh scattering. The flux can be generated by a suitable source, such as an effusion cell used during molecular beam epitaxy. The present device uses: a light source, such as a helium neon laser for generating a monochromatic coherent beam of light; a source for emitting a flux of atoms or molecules; a high precision mirror assembly capable of providing a sufficient number of reflections though the flux beam to produce a detectable interference pattern; and an interference pattern detector to track the changes in flux.

BACKGROUND OF THE INVENTION

There are various techniques available for depositing high purity materials on substrates by either atomic or molecular growth. Such techniques include, but are not limited to, molecular beam epitaxy (MBE), chemical beam epitaxy (CBE), chemical vapor deposition (CVD), organometallic CVD (OMCVD), plasma enhanced CVD (PECVD), physical or RF sputtering, and laser ablation. All of these techniques require an adequate means for measuring the rate and composition of the material being deposited. The ideal means for such measurements is a flux monitor. To illustrate the need for an improved flux monitor system, one can consider MBE, an established technique for fabricating high quality electronic and opto-electronic devices in both research and industrial environments. The advantages of MBE over other growth techniques include the ability to produce high purity materials with controlled composition, layer thickness, dopant concentrations, and structure. MBE growth is achieved by directing the output of one or more effusion cells onto a heated substrate in an ultra-high vacuum chamber. The effusion cell's output typically consists of atoms of the desired growth and doping constituents to be deposited. The rates at which the atoms fluxes are emitted determine the stoichiometry and growth rate of the substrate overlayers.

A high level of interest in MBE has been driven by the advantages that III–V and II–VI semiconductors have over silicon semiconductors namely, increased carrier mobilities, optical transitions, lattice matching and band gap engineering. The increased carrier (both hole and electron) mobilities enable devices fabricated from these other materials to operate with faster switching times than their silicon counterparts. The use of ternary and quaternary semiconductors allows exotic overlayers and multilayer structures to be grown and lattice matched to substrates, thus minimizing the stress and its effect on device properties. Band gap engineering, accomplished by altering the stoichiometry of ternary or quaternary semiconductors, is used to produce semiconductor lasers, high speed transistors, optical switches and other devices by creating population inversion layers, or sinks, or traps for carriers.

Exploiting the true potential of these advantages requires precise control over the stoichiometry and thickness of the deposited layers which, in turn, requires detailed knowledge of the amount of material being deposited and the rate at which it is deposited. Additionally, it would be extremely helpful to have these pieces of information while the sample is still being grown so that any corrections that need to be made to the fluxes can be made prior to removing the sample from the growth chamber for ex-situ analysis and testing.

Several different techniques are currently in use to monitor growth. These techniques are be either direct or indirect techniques. Direct techniques monitor what happens on the substrate as material is deposited, while indirect techniques monitor the material that is sent to the substrate.

Direct techniques include reflection high-energy electron diffraction (RHEED), ellipsometry, auger electron spectroscopy (AES), and x-ray photoelectron spectroscopy (XPS). These have the advantage that they directly determine either the amount of material deposited, or the surface composition. This is also their weakness. Such measurements are made after the material has been deposited, thereby making it impossible for a priori control of the deposition.

RHEED utilizes a grazing incidence, high energy (~10 keV) electron beam scattered from the target surface to produce an interference pattern on a phosphor screen. The symmetry of the diffraction pattern generated from what is essentially a two-dimensional crystal structure is very useful in tracking both the overall growth rate of the sample and the growth mode. Knowledge of the rate of growth and the growth mode allows calculation of the incident flux. The intensity of the zero-order spot can be monitored for oscillations produced by periodic variations in surface roughness produced when a new layer is grown. The period between oscillations is equal to that required to deposit a single monolayer (ML) of material assuming that the growth mode is layer-by-layer. For other growth modes, such as step flow or for very thick layers, the oscillations can be weak, or not present at all.

AES is commonly used for compositional determination in situ. AES uses a high energy (~10–15 keV) electron to ionize an atom to remove a core electron. A second electron decays into the core hole and imparts its energy to a third electron that escapes from the sample and is captured by an energy analyzer. This technique is very sensitive to local changes in the chemical environment and is used to detect not only the species present but also its bonding arrangement. This process relies on multiple electron transitions to generate a signal, and because of this, the signal strength is relatively small. To offset this small signal the detector must be placed in close proximity to the sample and long acquisition times (10+ seconds) are required. Positioning the detector in close proximity to the sample results in material being deposited on the detector which alters the measured kinetic energies of the ejected electrons and eventually causes it to fail. For these reasons AES analysis is typically done outside of the main growth chamber.

Photoemission spectroscopy is very similar to AES, it utilizes a beam of monochromatic x-rays to probe tightly bound core electrons. The photoemitted electrons escape from the sample and are collected in an energy dispersive spectrometer like that used in AES. Their energy is characteristic of both the species from which they were emitted and their local chemical environment. Differences in binding energies allow differentiation between surface and bulk atoms and provide insight into their bonding configuration. XPS can readily identify compositional changes on the order of 1%. The disadvantage of this method, in addition to problems associated with the detector discussed above, is that the electrons emitted can have high kinetic energies, thus giving them long escape depths that decreases the surface sensitivity of the technique.

Another conventional technique, ellipsometry, utilizes a laser beam, or light from a high pressure Xe lamp that passes through a polarizer and is incident on the surface at or near Brewsters angle. The reflected beam passes through a rotating analyzer and is detected. The ratio of reflection coefficients, as a function of ellipsometric angle, is determined. The data is presented by graphing the real component versus the imaginary components of the ratio. Ellipsometry relies on the difference between the refractive index of the overlayer and that of the substrate. For this reason, ellipsometry is ineffective for determination of growth of homoepitaxial films, or other films, where the indexes of refraction are equal. Ellipsometry requires a long data acquisition time in order to obtain sufficient signal for reliable results, thereby rendering it unsuitable for use as a real-time control technique.

Indirect methods, such as conventional optical flux monitoring (OFM), utilize atomic absorption and are capable of determining the flux of the incident material. Multiple monochromatic beams are passed in front of the sample where the incident fluxes are quantified. This measures the atomic fluxes just prior to deposition—too late to control the composition of the initial layer. Additionally, the proximity of the sampling beam and the substrate means that atoms that do not stick to the surface are counted twice, once when they are incident on the substrate, and once after they have been re-emitted from the surface. The main drawback to this technique is that many of the atomic species used in growth of these materials do not have a strong absorption peak that corresponds to a wavelength attainable by conventional lamps.

While such conventional techniques are currently used with varying degrees of success, none of them is able to measure and control the flux of all of the different materials simultaneously in real time. Thus, there is a need in the art for a technique for measuring, in real time, atomic fluxes emitted, particularly from an effusion cell.

SUMMARY OF THE INVENTION

In accordance with the present invention there is provided an apparatus for monitoring the flux of at least one of atoms and molecules from a source of same in a deposition chamber, said apparatus comprising:

a) a light source for generating a beam of monochromatic coherent light;

b) a first elongated single mode optical fiber having a first terminal end positioned to receive said beam of light from said light source and a second terminal end to which said beam of light is carried through said fiber;

c) means for splitting said beam of light received from said second terminal end of said first optical fiber into a sample beam and a reference beam;

d) a deposition chamber and a first mirror surface disposed within said deposition chamber;

e) a second elongated single mode optical fiber having a first terminal end positioned to receive said sample beam from said splitting means and a second terminal end to which said sample beam is carried, said second terminal end being positioned inside of said deposition chamber;

f) a first optical lens assembly positioned within said deposition chamber to receive said sample beam from said second terminal end of said second optical fiber and to focus said sample beam onto said first mirror surface;

g) at least one source disposed within said deposition chamber for emitting a flux of at least one of atoms and molecules;

h) a second mirror surface disposed within said deposition chamber and positioned opposite that of said first mirror surface so that said sample beam is repeatedly reflected back and forth a sufficient number of times across said flux and between the two mirror surfaces to produce a detectable interference pattern;

i) a second optical lens assembly disposed within said deposition chamber and positioned to receive said sample beam after it is reflected back and forth across said flux a sufficient number of times;

j) a third elongated single mode optical fiber having a first terminal end for receiving said sample beam from said second optical lens assembly within said deposition chamber and a second terminal end to which said sample beam is carried, said second terminal end positioned outside of said deposition chamber;

k) a fourth elongated single mode optical fiber having a first terminal end positioned to receive said reference beam from said splitting means and a second terminal end to which said reference beam is carried;

l) means for combining said sample beam from said second terminal end of said third optical fiber and said reference beam from said second terminal end of said fourth optical fiber, thereby producing an interference pattern;

m) an interference pattern detector for detecting said interference pattern and generating a corresponding signal; and n) a computer for determining a flux reading from said signal produced by said interference pattern detector.

In a preferred embodiment of the present invention the deposition chamber is under a vacuum.

In another preferred embodiment of the present invention the coherent light source is selected from the group consisting of a laser or laser diode.

In still another preferred embodiment of the present invention the coherent light source is a helium neon laser.

In a preferred embodiment of the present invention the sample and reference beams are formed by use of a bifurcated single mode fiber.

In yet another preferred embodiment of the present invention the mirror assembly is comprised of two opposing end surfaces of a single crystal silicon wafer.

In still another preferred embodiment of the present invention the ultra high vacuum deposition chamber is a molecular beam epitaxy chamber.

In another preferred embodiment of the present invention the reflecting surfaces are distributed Bragg reflectors.

In yet another preferred embodiment of the present invention, the distributed Bragg reflector layers consist of alternating layers of silicon dioxide and silicon nitride.

In another preferred embodiment of the present invention, the interference pattern detector consists of either a photodiode array detector or a charge coupled device detector.

BRIEF DESCRIPTION OF THE FIGURE

The sole FIGURE hereof is a schematic diagram of an optical flux monitor system of the present invention using Rayleigh Scattering to measure atomic fluxes during molecular beam epitaxy. This FIGURE represents only one preferred embodiment of the present invention and is not to be taken as limiting in any way.

DETAILED DESCRIPTION OF THE INVENTION

The flux monitor of the present invention can be used to measure atomic and molecular fluxes generated during any technique for depositing high purity materials in a deposition or growth chamber. The terms "deposition chamber" and "growth chamber" can be used interchangeably herein and the chamber can be at any suitable pressure for the deposition technique. That is, it can be operated under vacuum conditions as well as relatively high pressure conditions. Non-limiting examples of deposition techniques that are suitable for the practice of the present invention include molecular beam epitaxy (MBE), chemical beam epitaxy (CBE), chemical vapor deposition (CVD), organometallic CVD (OMCVD or MOCVD), plasma enhanced CVD (PECVD), physical or radio frequency sputtering and laser ablation. Preferred is MBE. The flux monitor of the present invention, when used to measure the growth of high purity material on a substrate during a technique like MBE, can be mounted between the effusion cell and its shutter in a vacuum chamber. This affords several advantages, the most important of which is the ability to control the flux from the effusion cell before, or during, its deposition onto the target substrate. This arrangement will also help to minimize thermal transients associated with shutter operation because it provides a buffer region. Also, the fact that the flux monitor is relatively far away from the sample (target substrate) minimizes problems that can occur with monitoring errors associated with re-emission from the target (substrate) surface.

The flux monitor of the present invention uses Rayleigh scattering. Rayleigh scattering is elastic scattering of light from small particles whose diameter is less than 5% of the incident radiation wavelength. The theory of Rayleigh scattering is described in J. D. Ingle Jr. and S. R. Crouch, *Spectrochemical Analysis,* Prentice Hall, Englewood Cliffs, N.J. 1988 and B.Chu, *Laser Light Scattering,* Academic Press New York, 1974, both of which are incorporated herein by reference. The incident photons polarize the electron clouds surrounding an atom inducing a dipole momment that allows the atom to absorb energy exciting it to a very short lived virtual level. The decay of the electron from this virtual level re-emits a photon of the same energy in a random direction. In the practice of the present invention, Rayleigh scattering is used to measure the scattering from a volume containing a large number of particles, instead of measuring the scattering from a single particle. Thus, by integrating over all scattering angles one can determine the scattering-to-transmission ratio wherein a change in refractive index is directly proportional to the number of atoms encountered. This can be done in molecular beam epitaxy because one is operating at extremely low pressures (typically on the order of $5 \times 10^{-9}$ torr) where the interactions between atoms can be neglected and the materials act like ideal gases. The change in polarization is proportional to the molecular weight of the atoms, but it does not significantly affect the lifetimes of the virtual states. For this reason, Rayleigh scattering can be used to determine the molecular weights of small molecules in dilute solutions.

The creation of virtual states by the interaction between the photons and atoms produces a net decrease in the photon wave front propagation rate. This decrease in rate is proportional to the number of atom-photon interactions. The overall decrease in the propagation rate defines the index of refraction for any medium. The index of refraction can be defined by:

$$\eta_i = \frac{c}{c_i}$$

where c is the speed of light in a perfect vacuum and $c_i$ is the speed of light in the medium of interest. Thus, light travels more slowly through materials with high indexes of refraction.

The relationship between the change in refractive index and the change in phase between the sample beam and the reference beam can be described by determining the distance the two beams travel in an identical amount of time.

$$l_s = \frac{tc}{(\eta_i + \Delta\eta)}$$

$$l_r = \frac{tc}{\eta_i}$$

where
   $l_s$ is the distance traveled by the sample (reference) beam
   t is the time interval
   c is the speed of light
   $\eta_i$ is the index of refraction in the sampling region
   $\Delta\eta$ is the change in index produced the atomic interactions.

An increase in index of refraction reduces distance traveled by the sample beam as compared to that traveled by the reference beam. The difference between these two distances, $\Delta l$, can be shown to be $$\Delta l = \frac{l_r \Delta\eta}{(\eta_i + \Delta\eta)}.$$

The detector suitable for use in the present invention operates by using a beam splitter to overlap these two beams and observing the resulting interference pattern. Changing the phase angle between the two beams causes a corresponding change in the interference pattern. Tracking these changes allows the determination of both the direction and magnitude of the phase shift. If one defines the origin at the midpoint between the centers of the two beams one can characterize the intensity at this point in terms of the phase angle between the two beams by $$I(\phi) = I_0 \cos(\phi)$$

where $I_0$ is the incident intensity of the two beams at that point and $\phi$ is the phase angle between the two beams.

The phase angle can be related to the difference in length by $$\phi = \frac{\Delta l}{\lambda}$$

where $\lambda$ is the wavelength of the monochromatic coherent light.

The total number of fringe shifts observed when for a given change in index of refraction is equal to the phase angle divided by the periodicity of the function.

The sole FIGURE hereof represents a preferred embodiment flux monitor apparatus of the present invention used for molecular beam epitaxy measurements. A light source 2 is used to generate a monochromatic coherent light beam. It is to be understood that the terms light beam and energy beam can be used interchangeably herein. It is preferred that the coherent light source be a laser or laser diode. The wavelength of the light is not critical to the practice of this invention. It is more preferred that the coherent light source be a helium neon laser (632.8 nm) such as research model number 79200 that is manufactured by Oriel Corporation of Stratford, Conn. The light passes through a "laser-to-fiber optic" coupler 4 and travels through single mode optical fiber 6 to a means 8 for splitting said light beam into a sample beam and a reference beam. The sample beam enters first terminal end of optical fiber 10 where it passes through a "feedthrough device" 11 at flange 13 and is carried into vacuum chamber 16 at the second terminal end of optical fiber 10. It is preferred that the single mode optical fibers be graded index optical fibers. Single mode optical fibers are preferred because they help preserve the gaussian profile of the TEM$_{00}$ laser beam mode in order to produce an interference pattern that can be detected and measured. Although optical fibers are the preferred means for carrying the light beams from one element to another in the flux monitor, it is to be understood that any other suitable means may also be used. For example, in some applications the beam can merely be transmitted through the air to its intended target.

In another incarnation, the monitor can be used with a fast response, single element photodiode to track high pressure transient phenomena. An example of this type of phenomenon would be the pressure wave generated by the deflagration or detonation of an explosive charge. In this application, the time dependence of the pressure swing measured by the sensor would be the most important parameter. The only change to the equations governing the operation of the monitor stems from the non-linearity in the gas density versus pressure curve.

The means 8 for splitting said light beam can be any device suitable for splitting such a light, or energy, beam into two substantially equal beams. Non-limiting examples of devices that can be used for this purpose are optical fiber beam splitters and slits or parallel projection. Optical fiber beam splitters are preferred. It is more preferred that the beam splitter be a bifurcated fiber optic cable, such as those available from Wave Optics, Inc. of Mountain View, Calif. and manufactured by such companies as Hitachi Cable Manchester Inc. and Prestolite Wire Corporation. It is also understood that the terms "fiber optic", "optical fiber", and "fiber optic cable" can be used interchangeably herein.

The sample beam optical fiber 10 passes through a high vacuum compatible, high temperature fiber optic feedthrough at 11 in vacuum flange 13 attached to the vacuum chamber (MBE chamber) 16. The second terminal end of said optical fiber 10 carries the light beam to a collimating lens assembly 12 to reflect the light beam onto first mirror surface 14a of first mirror assembly 18a. Lens assembly is preferably comprised of a collimating lens and a reflecting mirror mounted to said mirror assembly 18a. In a preferred embodiment of the present invention the reflecting mirror is a right angle prism reflector. Mirror assemblies 18a and 18b should be capable of producing a sufficient number of reflections of the laser beam through the flux beam 20 generated by molecular beam emitter 22. Non-limiting examples of emitters suitable for use in the present device are effusion cells, valved crackers, e-beam evaporators, and the like. The large number of reflections is needed to produce a sufficiently long path length in a confined space to generate an interference pattern that is detectable. That is, the larger the laser beam path length in the free space portion 24, the greater the sensitivity of the detector. Thus, by "effective number of reflections", we mean at least that number of reflections needed to produce a detectable interference pattern shift for the expected flux fluctuations. For example, a typical path will be about 5 m and thus will require at least abou 150 reflections, preferably at least about 200 reflections. It is preferred that a reflectivity of at least about 99% be achieved in order to maintain sufficient laser intensity to produce the desired interference pattern. Such values can be achieved by deposition of distributed Bragg reflectors on the mirror surfaces. Distributed Bragg reflectors consist of multiple pairs of thin layers of two materials with dissimilar indexes of refraction. The exact layer thickness and number of layers required is determined by the wavelength of the incident radiation and the index of refraction of the two materials. A preferred embodiment of this flux monitor uses $Si_3N_4/SiO_2$ layers, that can achieve reflectivities of 99.9%. A preferred method of providing mirror surfaces suitable for use in the present invention is to cut or cleave a silicon wafer in a way that will result in newly exposed end surfaces that are substantially perfect mirrors. The silicon wafer can be of any thickness that can be successfully cleaved, but it is preferred that the thickness be about 3 mm in order to ease the restraints placed on the mirror face alignment while minimizing thermal gradients across its two faces.

The sample beam, after passing through the flux beam the desired number of times is passed through a focusing lens assembly 26 into a first terminal end of the receiving optical fiber 28 which passes through a feedthrough 11 at flange 13 and terminates at a second terminal end outside of said vaccum chamber at coupling 30 on beam splitter 32. Beam splitter 32 recombines the sample beam from optical fiber 28 and reference beam that is carried through optical fiber 9 to coupling 34. The recombining of the sample beam and the reference beam produces an interference pattern 36 that is projected onto a photosensitive detector 38. The photosensitive detector measures changes in the interference pattern 36 which is altered by fluctuations in flux from the effusion cell in the vacuum system (MBE chamber). These fluctuations alter the refractive index of the medium through which the sample beam passes. This alters the speed of the light passing through one leg of the interferometer relative to the reference leg and will produce a change in the phase angle between the two beams that produces a shift in the interference pattern. The photosensitive detector can merely be a screen onto which the overlapping beams are projected and the resulting interference pattern observed by eye. In a preferred embodiment of the invention, the photosensitive detector is typically a 1- or 2-dimensional photodiode array detector that will have numerous channels that are capable of converting the photon intensity to voltage signals to enable the detection of minute changes in the interference pattern. Typical multi-element photosensitive detectors include, but are not limited to photodiode array detectors and charge-coupled detectors.

It is also within the scope of this invention to pass the output from the photodetector through an analog-to-digital converter 40 and then to a computer 42. The computer 42 runs an algorithm capable of identifying the sinusoidal waveform produced by the interference of the two beams and keeps track of the shifts produced by changes in the phase angle between the sample and reference beams.

The computer algorithm can also be used to integrate the flux over time to determine total fluence. This output can be integrated into control software to open/close shutters and alter effusion cell temperatures to achieve the growth rate required.

While I have shown and described certain specific embodiments of the instant invention, it will be readily apparent that many minor changes of structure and operation could be made without departing from the spirit of this invention.

What is claimed is:

1. An apparatus for monitoring the flux of at least one of atoms and molecules from a source of same, said apparatus comprising:
    a) a light source for generating a beam of monochromatic coherent light;
    b) a means for splitting said beam of light into a sample beam and a reference beam;
    c) a chamber containing a source for generating a path of one or both of atoms and molecules;
    d) a mirror assembly comprised of two opposing mirror surfaces for reflecting said sample beam across the path of one or both of atoms and molecules an effective number of times;
    e) a means for combining said sample beam and said reference beam, thereby producing an interference pattern;
    f) an interference pattern detector for detecting said interference pattern and generating a corresponding signal; and
    g) a computer for determing a flux reading from said signal produced by said interference pattern detector.

2. The apparatus of claim 1 wherein the chamber is a deposition chamber.

3. The apparatus of claim 1 wherein the monochromatic coherent light source is a laser.

4. The apparatus of claim 3 wherein the laser is a helium neon laser.

5. The apparatus of claim 1 wherein the mirror surfaces are end surfaces of a single crystal silicon wafer.

6. The apparatus of claim 1 wherein said interference pattern is produced as an analog signal.

7. The apparatus of claim 6 wherein an analog to digital converter is used to convert said analog interference pattern into its digital equivalent.

8. The apparatus of claim 6 wherein said interference pattern detector is a photosensitive detector.

9. The apparatus of claim 8 wherein said photosensitive detector is a one or two dimensional photodiode array detector.

10. An apparatus for monitoring the flux of at least one of atoms and molecules from a source of same in a deposition chamber, said apparatus comprising:
    a) a light source for generating a beam of monochromatic coherent light;
    b) a first elongated single mode optical fiber having a first terminal end positioned to receive said beam of light from said light source and a second terminal end to which said beam of light is carried through said fiber;
    c) means for splitting said beam of light received from said second terminal end of said first optical fiber into a sample beam and a reference beam;
    d) a deposition chamber and a first mirror surface disposed within said deposition chamber;
    e) a second elongated single mode optical fiber having a first terminal end positioned to receive said sample beam from said splitting means and a second terminal end to which said sample beam is carried, said second terminal end being positioned inside of said deposition chamber;
    f) a first optical lens assembly positioned within said deposition chamber to receive said sample beam from said second terminal end of said second optical fiber and to focus said sample beam onto said first mirror surface;
    g) at least one source disposed within said deposition chamber for emitting a flux of at least one of atoms and molecules;
    h) a second mirror surface disposed within said deposition chamber and positioned opposite that of said first mirror surface so that said sample beam is repeatedly reflected back and forth a sufficient number of times across said flux and between the two mirror surfaces to produce a detectable interference pattern;
    i) a second optical lens assembly disposed within said deposition chamber and positioned to receive said sample beam after it is reflected back and forth across said flux a sufficient number of times;
    j) a third elongated single mode optical fiber having a first terminal end for receiving said sample beam from said second optical lens assembly within said deposition chamber and a second terminal end to which said sample beam is carried, said second terminal end positioned outside of said deposition chamber;
    k) a fourth elongated single mode optical fiber having a first terminal end positioned to receive said reference beam from said splitting means and a second terminal end to which said reference beam is carried;
    l) means for combining said sample beam from said second terminal end of said third optical fiber and said reference beam from said second terminal end of said fourth optical fiber, thereby producing an interference pattern;
    m) an interference pattern detector for detecting said interference pattern and generating a corresponding signal; and n) a computer for determining a flux reading from said signal produced by said interference pattern detector.

11. The apparatus of claim 10 wherein said deposition chamber is a vacuum chamber.

12. The apparatus of claim 10 wherein said monochromatic coherent light source is a laser.

13. The apparatus of claim 12 wherein said laser is helium neon laser.

14. The apparatus of claim 10 wherein one or more of said first, second, third, or fourth of said elongated single mode optical fibers is a bifurcated optical fiber.

15. The apparatus of claim 10 wherein said splitting means is selected from an optical fiber beam splitter, slits, and parallel projection.

16. The apparatus of claim 15 wherein the splitting means is an optical fiber beam splitter.

17. The apparatus of claim 10 wherein said mirror surfaces are the end surfaces of a single crystal silicon wafer.

18. The apparatus of claim 10 wherein said first optical lens assembly is comprised of a collimating lens and a reflecting mirror.

19. The apparatus of claim 10 wherein said source for emitting said flux is an effusion cell.

20. The apparatus of claim 10 wherein said source for emitting said flux is a valved cracker.

21. The apparatus of claim 10 wherein said source for emitting said flux is an electron-beam evaporator.

22. The apparatus of claim 10 wherein said sufficient number of reflections is at least about 150.

23. The apparatus of claim 10 wherein said second optical lens assembly is comprised of a focusing lens and a reflecting mirror.

24. The apparatus of claim 10 wherein said interference pattern is produced as an analog signal.

25. The apparatus of claim 24 wherein an analog to digital converter is used to convert said analog interference pattern into its digital equivalent.

26. The apparatus of claim 24 wherein said interference pattern detector is a photosensitive detector.

27. The apparatus of claim 26 wherein said photosensitive detector is a screen onto which the interference pattern is projected.

28. The apparatus of claim 26 wherein said photosensitive detector is a one or two dimensional photodiode array detector.

29. An apparatus for monitoring the flux of atoms from one or more effusion cells during molecular beam epitaxy comprising:

a) a laser for generating a beam of monochromatic coherent light;

b) a first elongated single mode optical fiber having a first terminal end positioned to receive said beam of light from said light source and a second terminal end to which said beam of light is carried through said fiber;

c) an optical fiber beam splitter positioned to receive said beam of light from said second terminal end of said first optical fiber into a sample beam and a reference beam;

d) a vacuum chamber and a first mirror surface disposed within said vacuum chamber;

e) a second elongated single mode optical fiber having a first terminal end positioned to receive said sample beam from said splitting means and a second terminal end to which said sample beam is carried, said second terminal end being positioned inside of said vacuum chamber;

f) a first optical lens assembly positioned within said vacuum chamber to receive said sample beam from said second terminal end of said second optical fiber and to focus said sample beam onto said first mirror surface;

g) at least one effusion cell disposed within said vacuum chamber for emitting a flux of atoms;

h) a second mirror surface disposed within said vacuum chamber and positioned opposite that of said first mirror surface so that said sample beam is repeatedly reflected back and forth a sufficient number of times across said flux and between the two mirror surfaces to produce a detectable interference pattern;

i) a second optical lens assembly disposed within said vacuum chamber and positioned to receive said sample beam after it is reflected back and forth across said flux a sufficient number of times;

j) a third elongated single mode optical fiber having a first terminal end for receiving said sample beam from said second optical lens assembly within said vacuum chamber and a second terminal end to which said sample beam is carried, said second terminal end positioned outside of said vacuum chamber;

k) a fourth elongated single mode optical fiber having a first terminal end positioned to receive said reference beam from said splitting means and a second terminal end to which said reference beam is carried;

l) means for combining said sample beam from said second terminal end of said third optical fiber and said reference beam from said second terminal end of said fourth optical fiber, thereby producing an interference pattern;

m) a photosensitive detector for detecting said interference pattern and generating a corresponding signal; and n) a computer for determining a flux reading from said signal produced by said interference pattern detector.

30. The apparatus of claim 29 wherein said laser is helium neon laser.

31. The apparatus of claim 29 wherein one or more of said first, second, third, or fourth of said elongated single mode optical fiber is a bifurcated optical fiber.

32. The apparatus of claim 29 wherein said mirror surfaces are the end surfaces of a single crystal silicon wafer.

33. The apparatus of claim 29 wherein said first optical lens assembly is a comprised of a collimating lens and a reflecting mirror.

34. The apparatus of claim 29 wherein said sufficient number of reflections is at least about 150.

35. The apparatus of claim 29 wherein said second optical lens assembly is comprised of a focusing lens and a reflecting mirror.

36. The apparatus of claim 29 wherein said interference pattern is produced as an analog signal.

37. The apparatus of claim 29 wherein an analog to digital converter is used to convert the analog interference pattern into its digital equivalent.

38. A method for monitoring a flux of at least one of atoms and molecules from a source in a deposition chamber, which method comprises:

a) generating a monochromatic coherent beam of light;
b) splitting said monochromatic coherent beam of light into a sample beam and a reference beam;
c) passing said sample beam of light through a flux of said at least one of atoms and molecules an effective number of times;
d) combining said sample beam and said reference beam of light thereby producing an interference pattern;
e) detecting said interference pattern with an interference pattern detector and generating a corresponding signal; and
f) determining a flux reading from said signal by feeding said signal into a computer running software suitable for interpreting said signal.

39. The method of claim 38 wherein the deposition chamber is a vacuum chamber.

40. The method of claim 38 wherein said monochromatic coherent light source is a laser.

41. The method of claim 38 wherein the beam is split by use of optical fiber beam splitter.

42. The method of claim 38 wherein said the sample beam is passed through said flux by use of two opposing mirror surfaces.

43. The method of claim 42 wherein said mirror surfaces are the end surfaces of single crystal silicon wafers.

44. The method of claim 38 wherein said source for emitting said flux is an effusion cell.

45. The method of claim 38 wherein said source for emitting said flux is a valved cracker.

46. The method of claim 38 wherein said source for emitting said flux is an electron-beam evaporator.

47. The method of claim 38 wherein said sufficient number of reflections is at least about 150.

48. The method of claim 38 wherein said interference pattern is produced as an analog signal.

49. The method of claim 47 wherein an analog to digital converter is used to convert said analog interference pattern into its digital equivalent.

50. The method of claim 38 wherein said interference pattern detector is a photosensitive detector.

51. The method of claim 50 wherein said photosensitive detector is a screen onto which the interference pattern is projected.

52. The method of claim 50 wherein said photosensitive detector is a one or two dimensional photodiode array detector.

* * * * *